(12) United States Patent
Guenther

(10) Patent No.: US 8,397,403 B2
(45) Date of Patent: Mar. 19, 2013

(54) RESILIENT SUPPORT

(75) Inventor: Norbert Guenther, Parsdorf (DE)

(73) Assignee: Gottinger Handelshaus GBR, Zorneding (DE)

( * ) Notice: Subject to any disclaimer, the term of this patent is extended or adjusted under 35 U.S.C. 154(b) by 392 days.

(21) Appl. No.: 12/528,057

(22) PCT Filed: Feb. 13, 2008

(86) PCT No.: PCT/DE2008/000272
§ 371 (c)(1),
(2), (4) Date: Aug. 20, 2009

(87) PCT Pub. No.: WO2008/101472
PCT Pub. Date: Aug. 28, 2008

(65) Prior Publication Data
US 2010/0101118 A1  Apr. 29, 2010

(30) Foreign Application Priority Data

Feb. 23, 2007 (DE) .......................... 10 2007 008 933
Mar. 22, 2007 (DE) .......................... 10 2007 013 823
Oct. 26, 2007 (DE) .......................... 10 2007 051 652

(51) Int. Cl.
*A43B 7/14* (2006.01)
(52) U.S. Cl. .................................. 36/88; 36/27; 36/140
(58) Field of Classification Search ............... 36/88, 7.8, 36/140, 109, 89, 23, 27; 602/23, 27
See application file for complete search history.

(56) References Cited

U.S. PATENT DOCUMENTS

| | | | |
|---|---|---|---|
| 1,354,427 A | 9/1920 | Welter | |
| 2,444,839 A | 7/1948 | Markkula | |
| 2,582,910 A * | 1/1952 | Lyon | 36/109 |
| 2,847,991 A * | 8/1958 | Andrews | 602/28 |
| 4,294,238 A * | 10/1981 | Woodford | 602/23 |
| 4,825,856 A * | 5/1989 | Nelson | 602/27 |
| 5,088,479 A * | 2/1992 | Detoro | 602/27 |
| 5,090,138 A * | 2/1992 | Borden | 36/102 |
| 5,460,600 A * | 10/1995 | Bieling | 602/27 |
| 5,475,935 A * | 12/1995 | Frost | 36/89 |
| 6,102,881 A * | 8/2000 | Quackenbush et al. | 602/28 |
| 6,302,858 B1 * | 10/2001 | DeToro et al. | 602/5 |
| 6,792,700 B2 * | 9/2004 | Gallegos | 36/89 |
| 6,792,703 B2 * | 9/2004 | Cohen | 36/136 |
| 6,793,638 B1 * | 9/2004 | DeToro et al. | 602/23 |
| 6,793,640 B1 * | 9/2004 | Avon | 602/23 |
| 7,219,450 B2 * | 5/2007 | Langley | 36/89 |
| 7,335,177 B2 * | 2/2008 | Reynolds et al. | 602/23 |
| 7,682,322 B2 * | 3/2010 | Engelman | 602/16 |

(Continued)

FOREIGN PATENT DOCUMENTS

| | | |
|---|---|---|
| DE | 1140312 | 11/1962 |
| DE | 10305131 | 9/2004 |

(Continued)

OTHER PUBLICATIONS

Gottinger GmbH, "Medizinisches Verordnungsprogramm" (Medical Prescriptive Program) (2007) (32 pages).

(Continued)

*Primary Examiner* — Marie Patterson
(74) *Attorney, Agent, or Firm* — Boyle Fredrickson, S.C.

(57) ABSTRACT

The invention discloses a resilient support having a slit in the heel part.

18 Claims, 5 Drawing Sheets

U.S. PATENT DOCUMENTS

| | | | |
|---|---|---|---|
| 8,062,243 B2 * | 11/2011 | DeToro et al. | 602/16 |
| 2005/0273028 A1 * | 12/2005 | Reynolds et al. | 602/27 |
| 2006/0264795 A1 | 11/2006 | Christensen | |
| 2007/0265557 A1 * | 11/2007 | Engelman | 602/23 |

FOREIGN PATENT DOCUMENTS

| | | |
|---|---|---|
| DE | 102004030570 | 1/2006 |
| DE | 202005021052 | 2/2007 |
| EP | 1714623 | 10/2006 |
| GB | 842961 | 8/1960 |
| WO | 2004/069087 | 8/2004 |

OTHER PUBLICATIONS

English Translation of German Official Letter dated Dec. 14, 2009, 3 pages.

* cited by examiner

RESILIENT SUPPORT

BACKGROUND OF THE INVENTION

1. Field of the Invention

The invention relates to a resilient support for a below-knee orthotic device for an articulated connection of a below-knee cuff to a foot cuff.

2. Description of the Related Art

Resilient supports of this type are employed, for instance, in below-knee orthotic devices for patients having deep paralyses, in the case of muscular illnesses, infantile cerebral pareses, pathologic illnesses, neurological changes or else with healthy individuals to support the function of the plantar flectors. By the below-knee orthotic device the foot is supported with respect to the lower leg, at the same time energy being absorbed by the resilient support during the step-on and standing phase and being released during the push-off phase.

The FIGS. 1 and 2 show a known resilient support as well as a below-knee orthotic device. The figures are based on the applicant's below-knee orthotic device SPRING and can be taken from the catalogue Medizinisches Verordnungsprogramm[1] by Gottinger GmbH, 85604 Zorneding. The below-knee orthotic device 2 includes a below-knee cuff 4 to encompass a lower leg 6 and a foot cuff 8 for fixing a foot 10. The two cuffs 4, 6 are articulated to each other via a resilient support 12 having a lower leg-side end portion 14 and a foot-side end portion 16, wherein the lower leg-side end portion 14 is accommodated in the below-knee cuff 4 and the foot-side end portion 16 is accommodated in a sole 18 carrying the foot 10. In order to assist the spring force, a heel part 20 of the resilient support 12 is curved in the opposite direction.

[1] Medical Prescription Range

What is a drawback of this known solution is that the spring rate of the resilient support is designed so that the best possible support is given in the push-off phase during walking. Due to the coordinated movement during walking the resilient support must develop a higher supporting force in the push-off phase than in the step-on phase, however, so that when making use of the known solution no "soft" step-on is possible and thus "the resilient support is pushed into the knees", which is annoying, or a strong rebound of the foot toward the knee takes place.

It is moreover a drawback that for executing an independent plantar flexion of the foot by muscle strength, as it is necessary, for instance, to operate the foot pedals when driving a motor vehicle, a patient must always apply a high counter-force due to the high spring rate so as to counteract the spring force of the resilient support.

It is the object of the present invention to provide a resilient support which eliminates the afore-mentioned drawbacks and is inexpensive to manufacture.

SUMMARY OF THE INVENTION

The objects are achieved by a resilient support comprising a lower leg-side end portion and a foot-side end portion interconnected via a heel part, wherein the resilient support has different spring rates in response to the angle of rotation ($\alpha$) of the foot, characterized in that in the heel area at least one slit is provided.

The resilient support according to the invention, for a below-knee orthotic device, for articulated connection of a below-knee cuff to a foot cuff includes a lower leg-side end portion and a foot-side end portion interconnected by a heel part, wherein the resilient support has different spring rates in response to the direction of movement (plantar/dorsal flexion) of the foot, because a slit is formed in the heel area. This has the advantage that in the case of plantar flexion taking place during step-on, the resilient support is softer and thus the foot steps on more softly and in the case of dorsal flexion, when the foot is pushed off, the resilient support is harder and supports the push-off.

The slit is preferably closed toward the lower leg-side and the foot-side end portions.

In an embodiment the slit is interwoven at its lower leg-side and foot-side slit ends, for instance by a Kevlar thread, whereby they are reliably closed and reinforced and the slit cannot be enlarged in an undefined way during operation and when using the resilient support.

It is the substantial advantage of the resilient support according to the invention that it includes superimposed layers which are separated by the slit, wherein they may have different thicknesses on which the spring rigidity of the resilient support depends. In order to facilitate manufacture, a separating film is preferably provided in the slit.

In support of the spring effect of the resilient support the heel part can be curved in the opposite direction with respect to the lower leg-side and the foot-side end portions and can preferably be made of fiber-reinforced, for instance carbon fiber-reinforced, plastic material.

In a preferred embodiment, an insert member can be introduced into the slit, whereby the layers abutting during a dorsal extension can be damped.

In order to improve the damping, the material of the insert member can be a plastic material, for instance, especially an elastomer.

The insert member is preferably adhesively joined to the resilient support at an inner surface to prevent the insert member from changing its position during use of the resilient support. The outer surface of the insert member is free, whereby a clearance can be formed between the resilient support and the insert member.

In order to avoid, for instance in the case of material failure of the resilient support, injury of the patient using the resilient support, a protective member can be provided with the same.

The protective member is advantageously adhesively joined to the surface of the resilient support.

For instance, the protective member is arranged at the inside and the outside of the resilient support in the area of the lower leg-side end portion and the heel part, as high loads of the resilient support may prevail in this area.

These, and other aspects and objects of the present invention will be better appreciated and understood when considered in conjunction with the following description and the accompanying drawings. It should be understood, however, that the following description, while indicating preferred embodiments of the present invention, is given by way of illustration and not of limitation. Many changes and modifications may be made within the scope of the present invention without departing from the spirit thereof, and the invention includes all such modifications.

BRIEF DESCRIPTION OF THE DRAWINGS

Hereinafter preferred embodiments of the invention are illustrated by way of schematic drawings in which.

DETAILED DESCRIPTION OF THE PREFERRED EMBODIMENT

Figure 3:
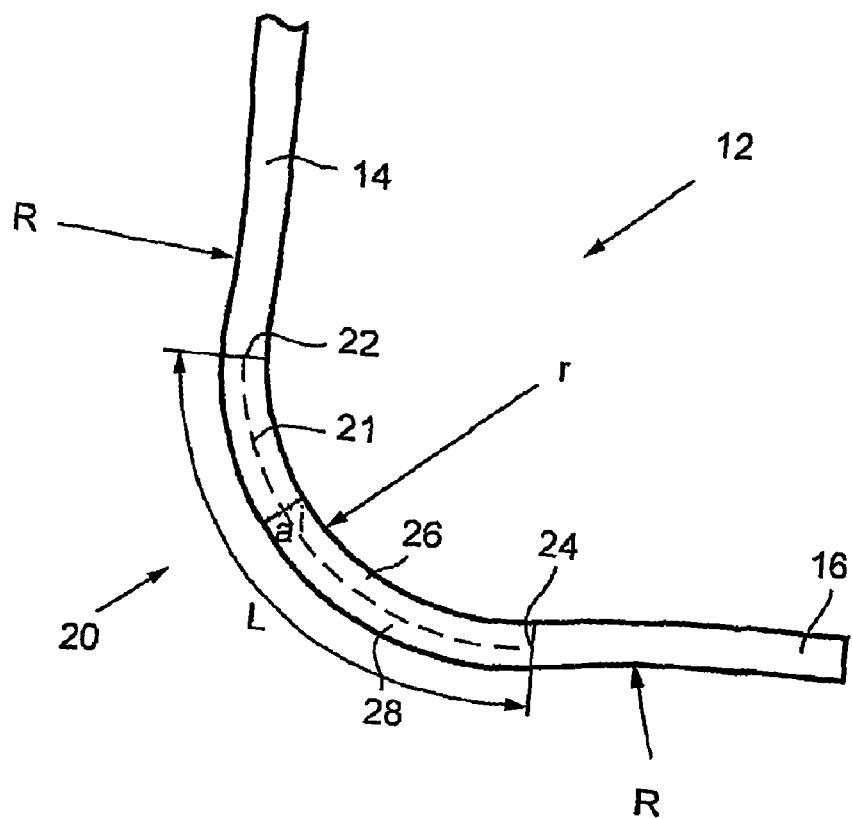
FIG. 3 is a side view of a resilient support according to the invention according to a first embodiment.

FIG. 3 shows a preferred embodiment of a resilient support 12 according to the invention. The resilient support 12 has an approximately L-shaped configuration including a lower leg-side end portion 14 and a foot-side end portion 16 which are interconnected by a heel part 20 curved in the opposite direction. The resilient support 12 is a leaf spring, wherein the material used preferably is a fiber-reinforced plastic material, for instance glass-fiber reinforced or carbon-fiber reinforced plastic material or composite material. This material excels, with minimum weight, by an excellent flexural rigidity and high fatigue resistance. On principle, also other suited materials can be used, however, which always have to be chosen with regard to minimum weight and maximum fatigue resistance.

In the heel area of the resilient support 12 a slit 20 is formed extending approximately centrally along the heel part 20 over the entire curved heel area and ending in the direction of the respective end portions 14, 16.

Figure 4:
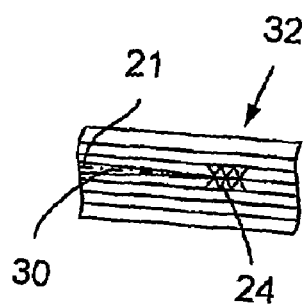
FIG. 4 is a side view of a slit area of the resilient support according to the first embodiment.

FIG. 4 shows a detailed representation of a slit end 24. During manufacture the not pre-impregnated tissue layers 32 are cut and laid on top of each other, wherein a separating film 30 extending over the entire length L of the slit 20 to the ends 22, 24 is inserted in the slit area. The areas adjacent to the separating film 30 are sown up with a Kevlar thread so that the film is fixed and the slit length is defined. After that, the multi-layer structure is impregnated with matrix resin and hardened in a tool.

As an alternative of manufacture, tissue layers 32 pre-impregnated with matrix resin can be used. The manufacturing steps of the resilient support 12 are the same, wherein the multi-layer structure is no longer pre-impregnated with matrix resin but only hardened.

After manufacture, the separating film 30 is retained in the slit, thus minimizing the friction during use of the resilient support 12 and increasing the fatigue resistance.

In order to realize different spring forces of the two layers 26, 28, it may be advantageous when they have different thicknesses a, i viewed in central direction. The overall thickness g of the resilient support 12 is substantially constant over its total length so that in each body portion 14, 16, 20 the formula g=a+i is applicable.

The curvature of the heel part 20 is formed by two radii R and r. The radius r and the part of the resilient support 12 extending to the below-knee cuff 4 (cf. FIGS. 1 and 2) substantially determine the flexibility of the resilient support 12 during plantar flexion, while the radius R primarily determines the flexibility of the resilient support 12 during dorsal extension (i.e., rotation of the foot about the ankle joint so that the dorsum of the foot approaches the lower leg front). As a rule, the resilient support 12 will be designed such that a dorsal extension is less supported, but primarily a plantar flexion is supported. The flexibility in this case is located in the area close to the ankle joint.

Figure 2:
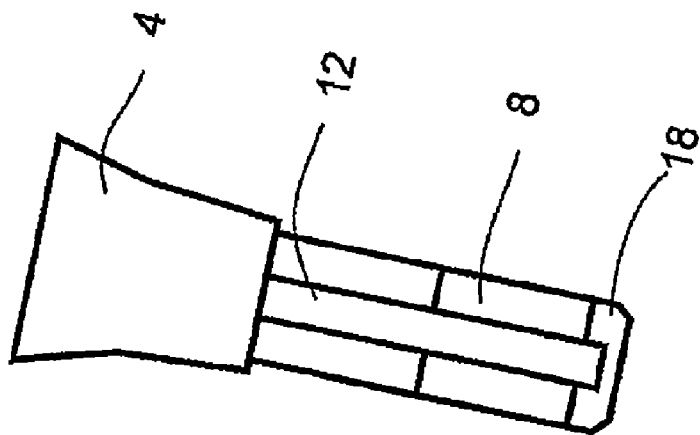
FIG. 2 is a view from rear of the known below-knee orthotic device illustrated in FIG. 1.
Figure 1:
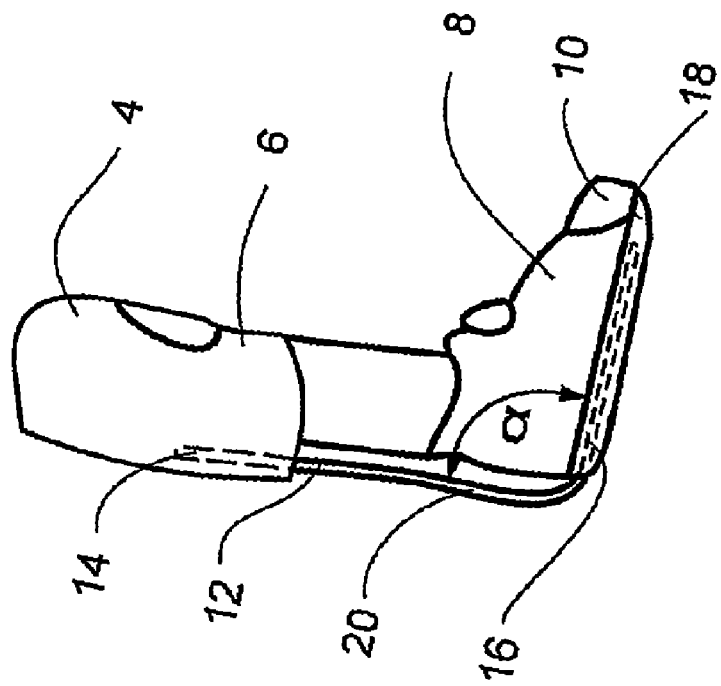
FIG. 1 is a side view of a known below-knee orthotic device including a known resilient support.

The below-knee cuff 4 and the foot cuff 8 are not substantially different from the state of the art according to FIG. 1 and FIG. 2 so that a repeated explanation is dispensed with.

The function and mode of action of the resilient support 12 according to the invention in combination with the below-knee orthotic device 2 shall be illustrated hereinafter:

The below-knee orthotic device 2 encompasses the lower leg 6 and the foot 10 of a patient by its below-knee cuff 4 and its foot cuff 8. The cuffs 4, 8 are articulated to each other via the resilient support 12 so that the patient is able to carry out dorsal extensions and plantar flexions with his/her foot 10 about the ankle joint and/or such movements are assisted.

The resilient support 12 is fixedly integrated at its end portions 14, 16 in the cuffs 4, 8.

Figure 5:
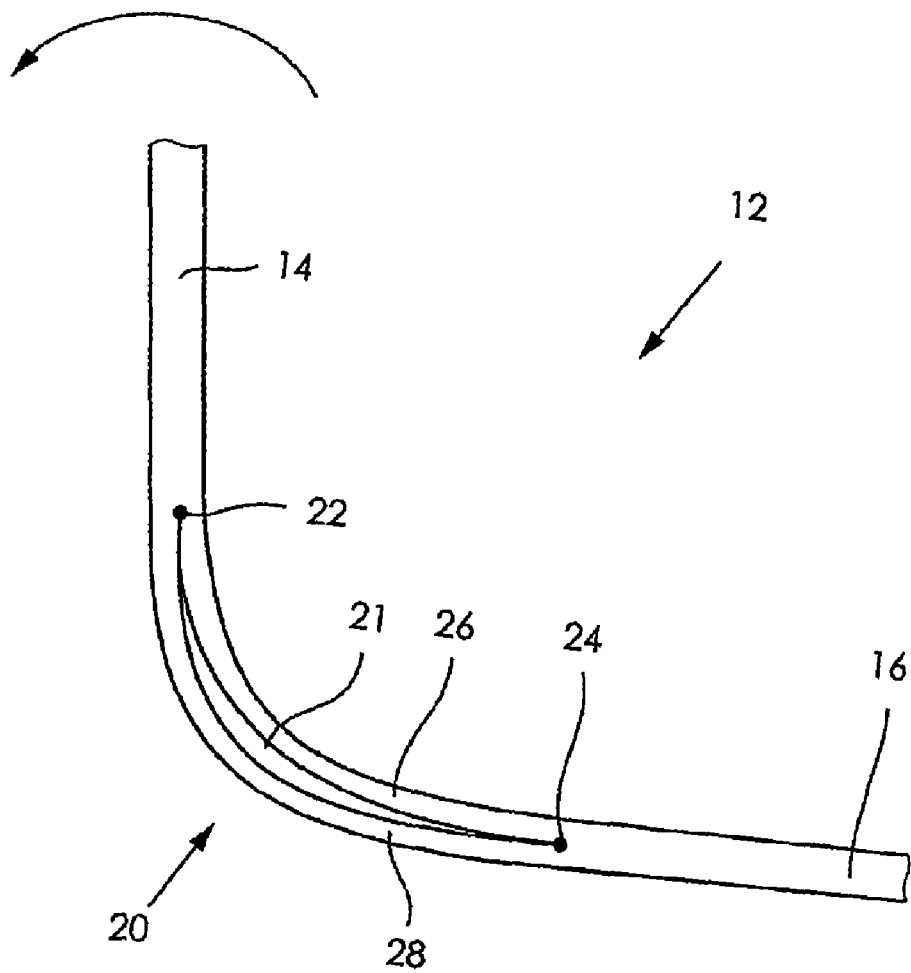
FIG. 5 is a side view of the slit area of the resilient support according to the first embodiment.

From a particular magnitude of the angle ($\alpha$) of the plantar flexion, the outer layer 28 bulges, as shown in FIG. 5, whereby the distance of the layers 26, 28 from each other is increased and thus the height of the slit 21 is enlarged. By the bulging of the outer layer 28 the spring tensions are shifted to the inner layer 26, whereby a higher tensile load is applied to the latter. The outer layer 28 is simultaneously relieved or loaded with flexural stress which is by far lower than the tensile load of the inner layer. The larger the angle ($\alpha$) of the plantar flexion, the lower the tensions become in the outer layer 28 and the higher become those in the inner layer 26. The load-bearing cross-section of the inner layer then defines the rigidity of the resilient support 12 which thus decreases. If the angle of plantar flexion is reduced, the bulging of the outer layer 28 decreases until the two layers 26, 28 are superimposed again. From this angle ($\alpha$) the resilient support 12 constantly has the maximum rigidity, as both layers absorb the spring tensions and are stretched. The spring rate is then determined by the cross-section of both layers.

Due to this dependence of the spring rigidity on the angle ($\alpha$) of the plantar flexion, the resilient support 12 exhibits a progressive spring characteristic whose spring rigidity decreases with increasing plantar flexion.

The function of a resilient support 12 in the individual walking phases is described in DE 103 05 131 B4 so that, to simplify matters, reference is made to the explanations given there.

Figure 6:
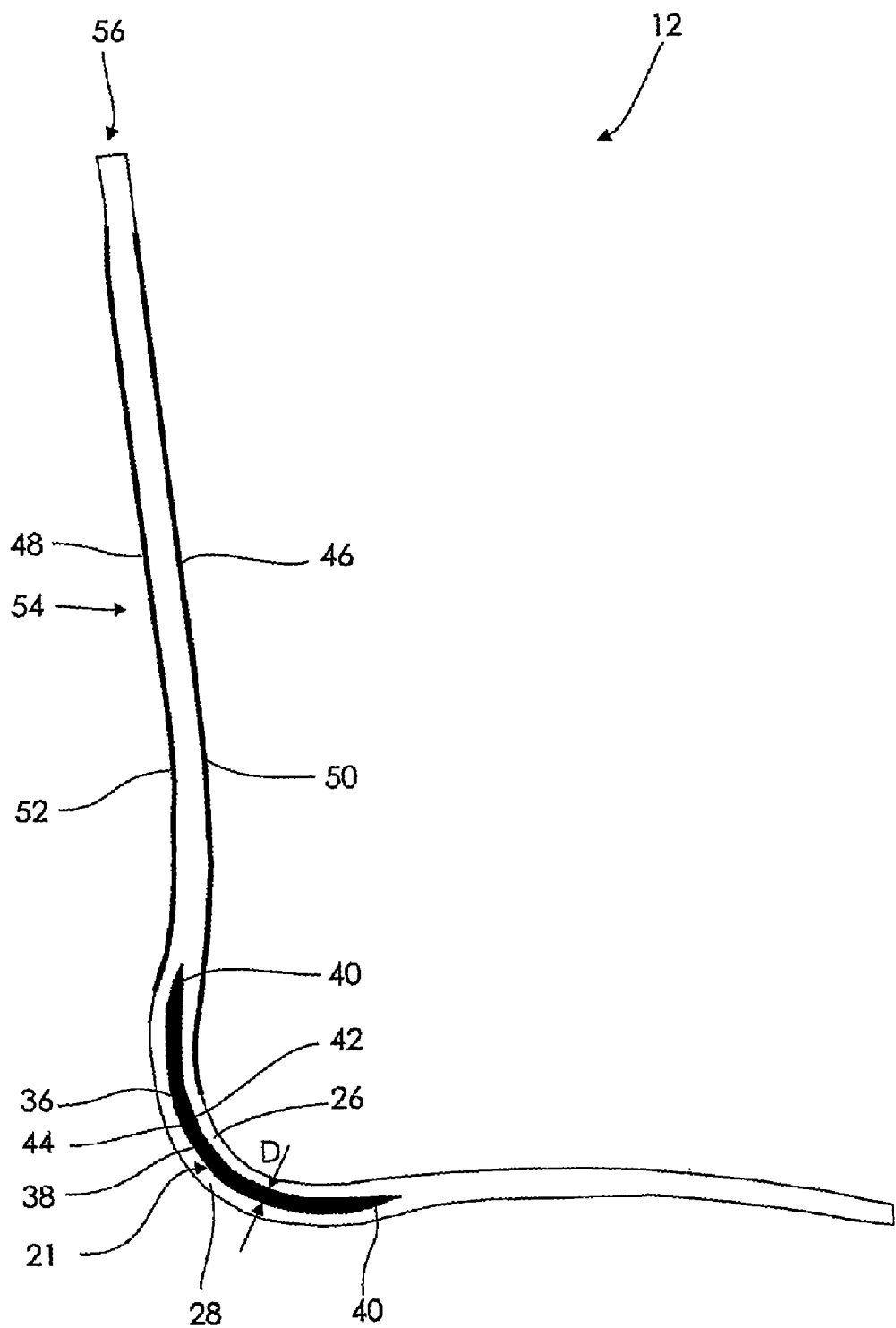
FIG. 6 is a side view of the slit area of the resilient support according to a second embodiment.

FIG. 6 shows a side view of the resilient support 12 according to a second embodiment. It includes an elastic insert member 36 made of an elastomer which is introduced into the slit 21 and substantially fills the same. The insert member 36 includes a central portion 38 having an approximately constant thickness D, for instance between 1 and 3 mm, and two tapered end portions 40. At an inner surface 42 the insert member 36 is adhesively joined to the inner layer 26 of the resilient support 12, on the other hand an outer surface 44 is separated from the outer layer 28 and is not joined to the same.

In use of the resilient support 12 the inner layer 26 and the outer layer 28 move apart during a plantar flexion, see also FIG. 5. Upon the subsequent dorsal extension they converge again at the afore-described resilient support, which entails a hard impact unless an insert member 36 is introduced in the slit 21. This impact results, for instance, in damages in the knee of a patient using a resilient support or else in an early material fatigue of the resilient support 12. In the embodiment according to FIG. 6, the elastic insert member 36 serves for damping the impact. In the case of plantar flexion a clearance is formed between the insert member 36 and the outer layer 28 with such a resilient support 12. In the subsequent dorsal extension the outer layer 28 then hits the elastic insert member 36 which exhibits progressive spring rigidity dependent on the Shore hardness and damps the impact, thereby treating the knee of the user of the resilient support with care.

In FIG. 6, at the resilient support 12 two protective members 46, 48 are arranged which prevent splitting out in the case of a material failure of the resilient support 12. The protective member 46 is fixed integrally to an inner surface 50 and the protective member 48 is fixed integrally to an outer surface 52 of the resilient support 12. The protective members extend approximately along a lower leg-side resilient support portion 54 of the resilient support 12 and end in the area of the heel part 20, the inner protective member 46 ending approximately in the center of the heel part 20 and the outer protective member 48 ending in the transition area between the resilient support portion 54 and the heel part 20. The protective members 46, 48 are somewhat spaced apart from a lower leg-side resilient support end 56 of the resilient support. The material of the protective members 46, 48 is extremely tough and is, for instance, an elastic plastic material which is vacuum-applied to the resilient support 12.

In the case of break of similar damage of the resilient support 12 the protective members 46, 48 prevent the material of the resilient support from splitting out which might hurt a user of the resilient support.

Instead of two protective members 46, 48 also one member can cover the resilient support 12 in sections or on the whole.

Figure 7:
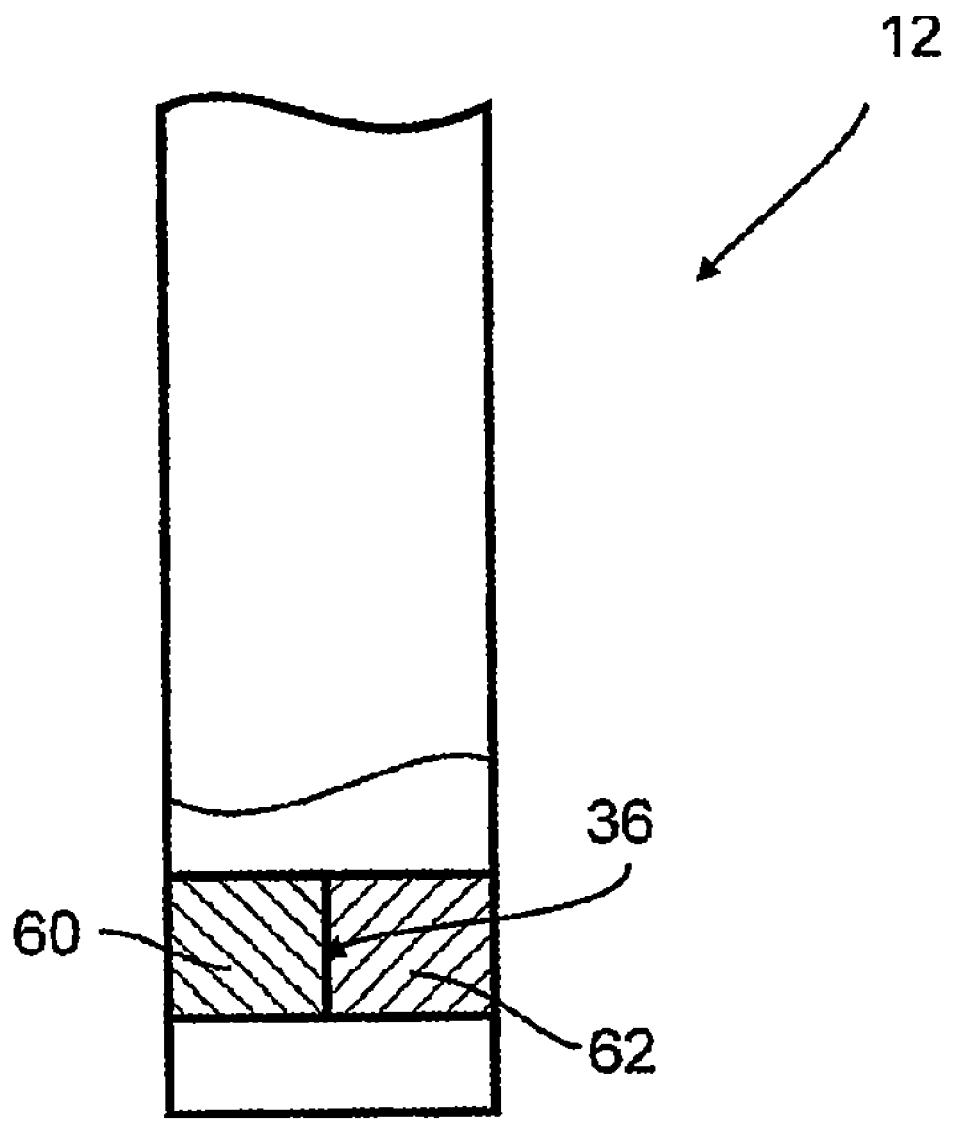
FIG. 7 shows a front view of the resilient support including a cut-out representation of the insert area according to the second embodiment.

FIG. 7 illustrates a front view of the resilient support 12 according to the second embodiment, wherein the area of the insert member 36 is cut out. The Shore hardness of the insert member 36 amounts to 65, for instance. It is also possible that it includes portions having a different Shore hardness. In the front view in FIG. 7, for example, the insert member 36 has two insert areas 60, 62 each having a width amounting to half of the total width of the resilient support 12. The insert area 60 on the left in FIG. 7 might have a higher Shore hardness than the other insert area 62, whereby during a dorsal extension the softer insert area 62 would cushion more easily than the harder one. This would entail the fact that the resilient support 12 is twisted and thus would have an additional degree of freedom for adaptation to particular walking characteristics of a patient using a resilient support.

The invention discloses a resilient support having a slit in the heel part.

Although the best mode contemplated by the inventors of carrying out the present invention is disclosed above, practice of the above invention is not limited thereto. It will be manifest that various additions, modifications and rearrangements of the features of the present invention may be made without deviating from the spirit and the scope of the underlying inventive concept.

The invention claimed is:

1. A resilient support for a below-knee orthotic device for an articulated connection of a below-knee cuff to a foot cuff, comprising:
a lower leg-side end portion and a foot-side end portion interconnected via a heel part, wherein the heel part includes at least one slit such that the resilient support has different spring rates in response to the angle of rotation ($\alpha$) of the foot,
wherein the heel part further includes at least two layers having the slit positioned between the two layers, the first layer being an inner layer proximate to the heel of the foot, the second layer being an outer layer distal from the heel of the foot.

2. A resilient support according to claim 1, wherein the slit is closed toward the lower leg-side and the foot-side leg portions.

3. A resilient support according to claim 2, wherein the slit has a lower leg-side slit end and a foot-side slit end each of which is interwoven or bonded.

4. A resilient support according to claim 1, wherein two superimposed layers having equal or different thicknesses (a, i) are formed by the slit.

5. A resilient support according to claim 1, wherein the slit is provided approximately in a neutral zone of the resilient support.

6. A resilient support according to claim 1, wherein the heel part is curved in the opposite direction with respect to the foot-side and lower leg-side end portions.

7. A resilient support according to claim 3, wherein the slit ends are interwoven with a thread having a high tensile strength-to-weight ratio.

8. A resilient support according to claim 1, wherein a separating film for separating the layers is provided in the slit.

9. A resilient support according to claim 1, wherein the resilient support is a leaf spring of fiber-reinforced plastic material.

10. A resilient support according to claim 9, wherein the leaf spring is made either of carbon fiber-reinforced plastic material, glass fiber-reinforced plastic material or another composite material.

11. A resilient support according to claim 1, wherein an insert member is introduced into the slit.

12. A resilient support according to claim 11, wherein the material of the insert member is a plastic material.

13. A resilient support according to claim 11, wherein the insert member is adhesively joined to the resilient support at an inner surface and is free at an outer surface.

14. A resilient support according to claim 11, wherein the insert member includes insert portions having a different Shore hardness.

15. A resilient support according to claim 1, wherein at least one protective member is arranged at the surface of the resilient support.

16. A resilient support according to claim 15, wherein the protective member is adhesively joined to the surface of the resilient support.

17. A resilient support according to claim 15, wherein the protective member is arranged at the inner surface and the outer surface of the resilient support in the area of the lower leg-side resilient support portion and the heel part.

18. A resilient support according to claim 12, wherein the plastic material is an elastomer.

* * * * *